(12) United States Patent
Ottonello et al.

(10) Patent No.: US 7,507,710 B2
(45) Date of Patent: Mar. 24, 2009

(54) ANTI-AMYLOID IMMUNOGENIC COMPOSITIONS, METHODS AND USES

(75) Inventors: Simone Ottonello, Parma (IT); Nadia Moretto, Parma (IT); Bruno Pietro Imbimbo, Parma (IT); Gino Villetti, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 11/709,280

(22) Filed: Feb. 22, 2007

(65) Prior Publication Data

US 2007/0224190 A1    Sep. 27, 2007

Related U.S. Application Data

(60) Provisional application No. 60/776,210, filed on Feb. 24, 2006.

(51) Int. Cl.
    *C07K 14/00* (2006.01)
(52) U.S. Cl. ............................. 514/2; 530/350
(58) Field of Classification Search ............ 514/2; 530/350
    See application file for complete search history.

(56) References Cited

FOREIGN PATENT DOCUMENTS

| WO | WO 2002/034777 | * | 5/2002 |
| WO | WO 2005/058940 | * | 6/2005 |

OTHER PUBLICATIONS

Krampert et al. 2000; Amyloidogenicity of recombinant human pro-islet amyloid polypeptide (ProIAPP). Chemistry & Biology 7:855-871.*

Moretto et al. 2007; Conformation-sensitive antibodies against Alzheimer amyloid-□ by immunization with a thioredoxin-contrained B-cell epitope peptide. Journal of Biological Chemistry 282(15): 11436-11445.*

* cited by examiner

*Primary Examiner*—Karen Cochrane Carlson
(74) *Attorney, Agent, or Firm*—Young & Thompson (57) ABSTRACT

The present invention provides a recombinant immunogenic obtained by tandem multimerization of a B-cell epitope bearing fragment of Aβ42, within the active loop site of a carrier (display site), preferably bacterial thioredoxin (Yrx). Polypeptides bearing multiple copies of Aβ42 fragments, preferably with an interposed amino acid linker, were constructed and injected into mice in combination with an adjuvant. Elicited antibodies were found to selectively bind to fibrillar and/or oligomers Aβ within neuritic AD plaques.

30 Claims, 3 Drawing Sheets

ANTI-AMYLOID IMMUNOGENIC COMPOSITIONS, METHODS AND USES

This application claims priority to provisional application no. 60/776,210, filed Feb. 24, 2006. The entire contents of the above-referenced application are hereby incorporated by reference in its entirety.

FIELD OF THE INVENTION

The present invention relates to immunogenic constructs comprising a fragment of Aβ42 and a carrier characterized in that said fragment is positioned within the active loop site (display site) of the carrier, method of production and uses of the same.

BACKGROUND OF THE INVENTION

Amyloidogenic diseases such as Alzheimer's disease (AD) have been recognized as the major cause of dementia in elderly people. The decline of cognitive abilities in AD is associated with histopathological changes in the brain, the most relevant being the formation of amyloid plaques and neurofibrillary tangles.

While amyloid plaques contain many proteins, they have as their main constituent the amyloid-β (Aβ) peptide. The formation of the Aβ peptide, and thereby Aβ amyloid plaques, arises from aberrant processing of the amyloid precursor protein (APP).

Currently, several pharmacological approaches have being developed to slow or reverse the progression of AD. While several approaches are directed to inhibit the metabolic generation of the Aβ peptide, others are directed to prevent the aggregation of the Aβ amyloid in the brain of AD affected patients.

However, the most promising approaches are directed to increase the brain clearance of Aβ plaques through the administration of either antigens able to generate an immune response against Aβ (active immunization) or antibodies directed against Aβ (passive immunization).

Antigens or immunogens are usually macromolecules that contain distinct antigenic sites or "epitopes" that are recognized and interact with the various components of the immune system. They usually comprise a small molecule or "hapten", such as short peptide, coupled to a suitable carrier. Carriers typically are proteins of higher molecular weight that are able to cause an immunological response when administered in vivo.

In an immune response, antibodies are produced and secreted by the B-lymphocytes in conjunction with the T-helper (TH) cells. In the majority of hapten-carrier systems, the B cells produce antibodies that are specific for both the hapten and the carrier. In these cases, the T lymphocytes will have specific binding domains on the carrier, but will not recognize the hapten alone. In a kind of synergism, the B and T cells cooperate to induce a hapten-specific antibody response.

Therefore, in constructing an effective antigen, the selection of the proper carrier and the proper hapten is crucial to guarantee a robust and selective immunogenic response. The safety of the antigen is also of crucial importance. For example, the administration to AD patients of the promising AN-1792 vaccine constituted by pre-aggregated Aβ42 and the immune adjuvant QS-21 led to severe meningoencephalitis in about 6% of the treated subjects. Both central activation of cytotoxic T cells and autoimmune reactions were proposed as potential mechanisms of toxicity. An immunological response against endogenous monomeric Aβ may be harmful since non-aggregated Aβ species have a physiological role in neuronal activity.

Thus, it is of great importance the proper selection of both the hapten and the carrier to guarantee antibody selectivity towards the harmful Aβ species and to prevent autoimmune toxicity.

WO2005058940 proposes conjugating peptide immunogen comprising Aβ peptide or a fragment thereof to a protein/polypeptide carrier.

The immunogenic constructs are produced by a chemical method comprising derivatizing functional groups of amino acid residues of the carrier wherein any unconjugated, derivatized functional groups of the amino acid residues are inactivated via capping to block them from reacting with other molecules. Such a method results in immunogens wherein the Aβ fragment is bound to the amino acid side chains of the carrier. While in WO2005058940 several different carriers and haptens have been proposed their in vivo histopathological efficacy has not been shown.

Kim, H. D. et al in Biochem. Biophys, Res. Commun. Volume 336, pages 84-92 propose an anti-Aβ DNA vaccine, composed of unscaffolded 11-fold repeats of Aβ1-6.

Such construct yielded antibodies that indiscriminately recognized monomeric, oligomeric and fibrillar Aβ42 species.

In general, selective targeting of immunogens against the different assembly states of Aβ42 (monomers, oligomers or fibrils) has not been achieved so far.

In view of the above considerations there is still a need to develop a safe and effective immunogenic construct which may be used in therapeuthic vaccination compositions to prevent the aggregation of Aβ amyloid in the brain of patients affected by AD or other amyloidogenic deseases such as Down Syndrome.

The present invention provides a recombinant immunogenic construct characterized in that the Aβ fragments is positioned within the active loop site (display site) of the carrier rather than bound to the ends of the carrier. Said peptide is obtained by tandem multimerization of a B-cell epitope bearing fragment of Aβ42, within the active loop site (display site) of a carrier, preferably thioredoxin (Trx).

The immunogens of the present invention were found to elicit antibodies recognizing neurotoxic oligomeric species of the Aβ amyloid which recently have been indicated as the most proximate causative agents of amyloidogenic diseases.

This capability has been associated with the construction of the immunogen featuring the Aβ amyloid within the carrier. Such configuration to some extent permits the right folding of the immunogenic protein and more effectively presents it to the immune system. When the immunogen bears more than one Aβ amyloid fragment, and in particular specific numbers of said fragments, the resemblance of the immunogen to the Aβ amyloid oligomers, is believed to further improve its efficacy as well as to increase the selectivity.

A linker between the carrier and the fragments further helps in preserving the peptide epitope assembly state.

SUMMARY OF THE INVENTION

The present invention provides an immunogenic construct (also indicated hereinafter as immunogen) comprising a fragment bearing the immunodominant B-cell epitope of Aβ42 and a carrier characterized in that said fragment is positioned within the active loop site (display site) of the carrier. The carrier is preferably thioredoxin whereas the Aβ fragment is advantageously a N-terminal fragment of less than 30 amino acid residues, preferably less than 20 amino acid, more preferably is Aβ1-15.

Even more preferably the immunogenic construct bears more than one fragment, preferably 2 to 16, most preferably 4 fragments.

The present invention also provides a method to construct said immunogen, the method comprising a linker assisted tandem multimerization of a B-cell epitope bearing a fragment of Aβ42 within the display of the carrier, preferably a N-terminal fragment of less than 30 amino acid residues.

In another aspect the present invention provides a composition comprising said immunogen for active vaccination against amyloidogenic diseases.

In a further aspect the present invention provides the use of said immunogen to develop antibodies, preferably monoclonal antibodies, to be used as passive vaccine against amyloidogenic diseases.

DESCRIPTION OF THE FIGURES

FIG. 2a-b-c show human brain sections treated with sera from mice immunized with immunogens according to the embodiments of the present invention.

DETAILED DESCRIPTION OF THE PREFERRED EMBODIMENTS

The present invention provides an immunogenic construct (or immunogen) comprising a carrier bearing at least one Aβ42 fragment. Said fragment is positioned within a surface exposed region (active loop site or display site) of the carrier which stabilizes it conformationally.

The exact size and chemical homogeneity of the construct is routinely determined by both gel electrophoresis and mass spectrometry.

The structure of the construct may be determined by analytical techniques; however nuclear magnetic resonance (NMR) is preferably employed.

The carrier is preferably thioredoxin (Trx). Trx is particularly suitable for its small size (109 amino acids), peptide display capacity, and ability to act as a non-toxic immunoenhancer capable of stimulating murine T-cell proliferation. However other carriers may be used.

The Aβ amyloid fragment is a N-terminal end, advantageously a N-terminal fragment having less than 30 amino acid residues, preferably less than 20 amino acid, and more preferably selected from the group consisting of Aβ1-3, 1-4, 1-5, 1-6, 1-7, 1-8, 1-9, 1-10, 1-11, 1-12, 1-13, 1-14, 1-15 reported in Table 1 below, according to the one-letter code for amino acids. Preferably, the Aβ amyloid fragment is Aβ1-15.

Advantageously the immunogenic construct of the invention bears more than one fragment, preferably from 2 to 16, more preferably 4 fragments.

In a preferred embodiment the fragments are bound to the carrier throughout a linker to prevent the formation of junctional epitopes. Said linker is a short amino acid sequence, preferably a linker constituted of 1 to 5 amino acid residues, more preferably Glycine-Glycine-Proline (Gly-Gly-Pro). However other linkers may be used, such as Glycine-Proline-Glycine-Proline-Glycine (Gly-Pro-Gly-Pro-Gly) (SEQ ID NO: 1), or Serine-Glycine-Serine-Glycine (Ser-Gly-Ser-Gly) (SEQ ID NO: 2).

The preferred immunogen construct consists of thioredoxin linked, optionally through a suitable linker, to four Aβ1-15 fragments, indicated hereinafter as Trx(Aβ1-15)$_4$.

The method to construct said immunogen is a cloning method that comprises amplifying the carrier in a suitable bacterium, inserting the carrier in a suitable vector, said vector comprising a T7 promoter for the protein expression throughout the pET system; preparing an Aβ fragment DNA insert; restricting and ligating the carrier-vector and the Aβ fragment DNA insert.

Preferably the Aβ fragment DNA insert comprises an amino acid linker.

Whenever multimers are prepared an excess of Aβ fragment DNA insert is employed.

TABLE 1

| Description | Sequence |
| --- | --- |
| Aβ1-3 | DAE |
| Aβ1-4 | DAEF (SEQ ID NO: 3) |
| Aβ1-5 | DAEFR (SEQ ID NO: 4) |
| Aβ1-6 | DAEFRH (SEQ ID NO: 5) |
| Aβ1-7 | DAEFRHD (SEQ ID NO: 6) |
| Aβ1-8 | DAEFRHDS (SEQ ID NO: 7) |
| Aβ1-9 | DAEFRHDSG (SEQ ID NO: 8) |
| Aβ1-10 | DAEFRHDSGY (SEQ ID NO: 9) |
| Aβ1-11 | DAEFRHDSGYE (SEQ ID NO: 10) |
| Aβ1-12 | DAEFRHDSGYEV (SEQ ID NO: 11) |
| Aβ1-13 | DAEFRHDSGYEVH (SEQ ID NO: 12) |
| Aβ1-14 | DAEFRHDSGYEVHH (SEQ ID NO: 13) |
| Aβ1-15 | DAEFRHDSGYEVHHQ (SEQ ID NO: 14) |

The preferred immunogenic construct of the present invention, upon injection once-a-month for 4 months in transgenic mice in which a brain β-amyloid pathology had been induced, appears to reduce the number and the size of Aβ plaques in hippocampus and cerebral cortex. Moreover the preferred immunogenic construct of the invention was found to elicit antibodies which recognize determined species of Aβ42.

Said antibodies upon intra-hippocampal injection are capable of clearing Aβ42-positive plaques in hippocampus and cortex of the transgenic mice, said clearing effect being particularly evident for oligomeric Aβ species. Said antibodies were also found to strongly improve Aβ-associated astrogliosis (Example 2).

Accordingly, the immunogenic constructs of the present invention may form compositions for use as both active and passive vaccine against amyloidogenic diseases.

For active vaccination, a pharmaceutical composition comprising the immunogenic construct of the invention is advantageously administered in combination with an adjuvant.

The selection of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Suitable adjuvants include 3 De-O-acylated monophosphoryl lipid A (MPL), muramyl-di-peptide and saponins such as QS21 and Quil A.

A preferred class of adjuvants is aluminum salts (alum), such as aluminum hydroxide, aluminum phosphate, aluminum sulfate. Further adjuvants include cytokines, such as interleukins (IL-1, IL-2, and IL-12), macrophage colony stimulating factor (M-CSF), tumor necrosis factor (TNF).

An adjuvant can be administered with the immunogen as a single composition, or can be administered before, concurrent with or after administration of the immunogen. Optionally, two or more different adjuvants can be used simultaneously.

Immunogen and adjuvant can be packaged and supplied either in the same vial or in separate vials and mixed before use.

The pharmaceutical compositions comprising the immunogenic construct of the invention may also include a variety of other pharmaceutically acceptable components. See Remington's Pharmaceutical Science (15$^{th}$ Ed., Mack Publishing Company, Easton, Pa., 1980).

The preferred pharmaceutical form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration.

The diluent is selected so as not to affect the biological activity of the combination. Examples of such diluents are distilled water, physiological phosphate-buffered saline, Ringer's solutions, dextrose solution, and Hank's solution.

For the parenteral administration, the immunogenic construct of the invention can be administered as injectable dosages of a solution or suspension of the substance in a physiologically acceptable diluent with a pharmaceutical carrier which can be a sterile liquid such as water oils, saline, glycerol, or ethanol.

Additionally, auxiliary substances, such as wetting or emulsifying agents, surfactants, pH buffering substances and the like can be present in the compositions.

The compositions of the invention may be prepared as injectables, either as liquid solutions or suspensions; solid forms suitable for solution in, or suspension in, liquid vehicles prior to injection can also be prepared.

The immunogenic construct of the invention may be administered in the form of a depot injection or implant preparation which can be formulated in such a manner as to permit a sustained release of the active ingredient.

Additional formulations suitable for other modes of administration include oral, intranasal, and pulmonary formulations, suppositories, and transdermal formulations.

For passive vaccination, the composition is injected into a mammal, such as a Guinea pig or other animal species and the resulting antibodies are purified and subsequently injected into humans.

Preferably the antibodies are monoclonal and are produced by immunizing a mammal with the Trx(Aβ1-15)$_4$ immunogenic construct. Said antibodies are used for the prevention and treatment of amyloidogenic diseases, in particular Alzheimer's disease.

EXAMPLE 1

Figure 1:
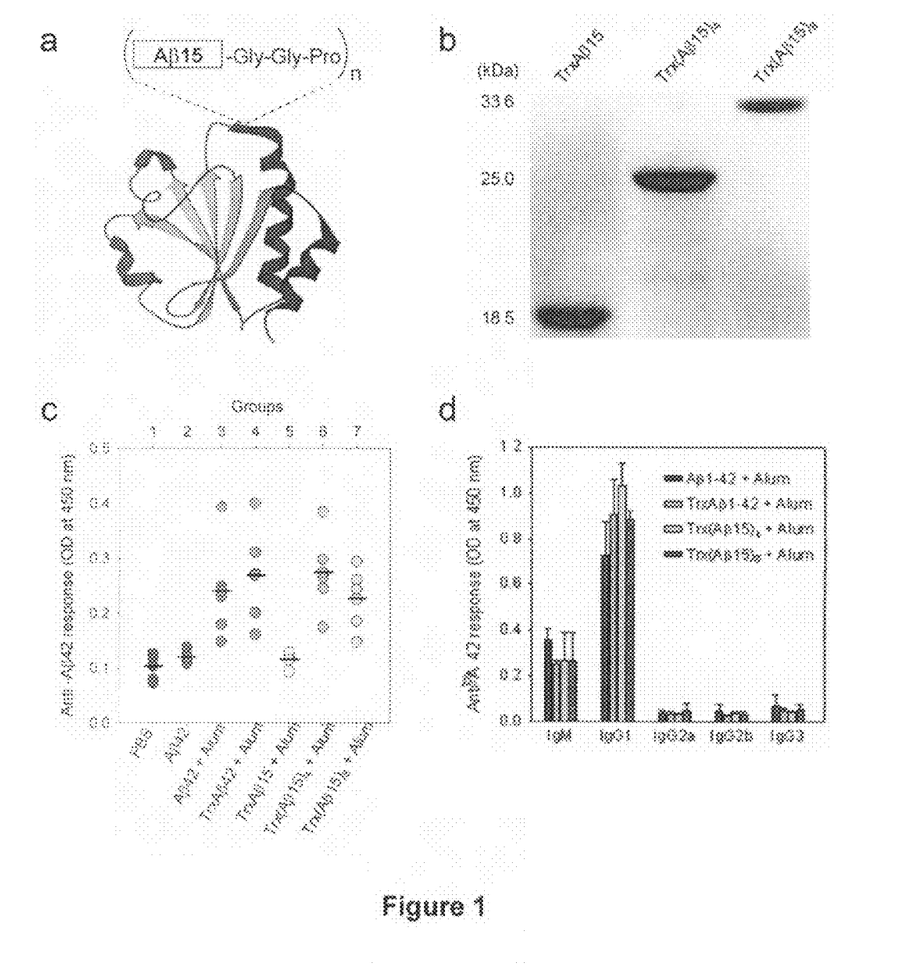
FIG. 1a shows the Trx(Aβ1-15-Gly-Gly-Pro)n construct according to the present invention.
FIG. 1b shows the purification to homogeneity by metal-affinity chromatography of constructs bearing one, four or eight copies of Trx-displayed Aβ1-15.
FIG. 1c shows anti-Aβ antibody levels elicited by immunogens according to embodiments of the present invention.
FIG. 1d shows Th2-polarized response immunogens according to embodiments of the present invention.

Preparation of Different TrxAβ Immunogenic Constructs and ex vivo Evaluation of the Effects of Different Anti-TrxAβ Antibodies A cloning strategy relying on the use of an excess of the Aβ1-15 DNA insert with respect to a modified recipient vector bearing the Trx coding sequence under the control of a phage T7 promoter was utilized for Trx(Aβ1-15)n construction (FIG. 1a). Constructs bearing one, four or eight copies of Trx-displayed Aβ1-15 were isolated and used to express the corresponding polypeptides, which were then purified to homogeneity by metal-affinity chromatography (FIG. 1b).

Instrumental to the production of properly assembled Aβ1-15 multimers were the directionality and in-frame fusion capability of the unique CpoI site present within the Trx sequence (nucleotide positions 99-105, corresponding to amino acid residues 34-35, identified as: 5' . . . CG/GT(A)CCG . . . 3') as well as the incorporation into Aβ1-15 DNA of a terminal sequence coding for an intervening Gly-Gly-Pro linker, thus also preventing the formation of junctional epitopes.

A fourth construct (TrxAβ42) bearing a single copy of the full-length Aβ42 peptide was prepared in a similar way. While all Trx(Aβ1-15)n polypeptides were soluble regardless of Aβ1-15 multiplicity, most of the TrxAβ42 protein ended up in inclusion bodies in an insoluble form (not shown). Thus, Aβ42 appears to be poorly soluble even when fused to Trx in the heterologous context of bacterial cells.

Five groups of 10 male BALB/c mice were treated with 10 nmol of the above Trx(Aβ15)n polypeptides, or with equivalent amounts of pre-aggregated synthetic Aβ42 or TrxAβ42, all supplemented with alum, an adjuvant approved for human use (FIG. 1c).

Two additional groups injected with buffer alone (PBS) or with alum-free Aβ42 served as negative controls. Sera were collected two weeks after the fourth injection, randomly pooled in pairs, and analyzed with Enzyme-Linked Immunosorbent Assay (ELISA) using aggregated Aβ42 as the target antigen. As shown in FIG. 1c, mean anti-Aβ antibody levels elicited by Trx(Aβ1-15)4 and Trx(Aβ1-15)8, but not by TrxAβ1-15, were significantly higher (P<0.05) than those of mock-treated controls and similar to those of the Aβ42-treated groups, where TrxAβ42 performed as well as free Aβ42.

P is the p-value associated with the t-test on log transformed control and experimental data using the Bayesian or regularized standard deviations; P indicates the probability that the result obtained in a statistical test is due to chance rather than a true relationship between measures.

A strongly anti-inflammatory Th2-polarized response, typical of the alum adjuvant, was revealed by isotype profiling (FIG. 1d). Although a prevalence of immunoglobulin of class G and subclasses 1 (IgG1) was observed with all antigens, the IgG1/IgG2 (immunoglobulin of class G and subclasses 2) a ratio was reproducibly higher (P<0.05) for multimeric Trx(Aβ1-15)n and TrxAβ42 immunoconjugates than for unconjugated Aβ42.

The ability of antisera generated in response to Trx(Aβ1-15)n to bind amyloid plaques was investigated next. This property, presently considered as the best prognostic indication of in vivo anti-Aβ antibody efficacy, is not shared by all previously described anti-Aβ antisera (e.g., m266 and other antibodies targeting the C-terminal portion of Aβ42).

Figure 2:
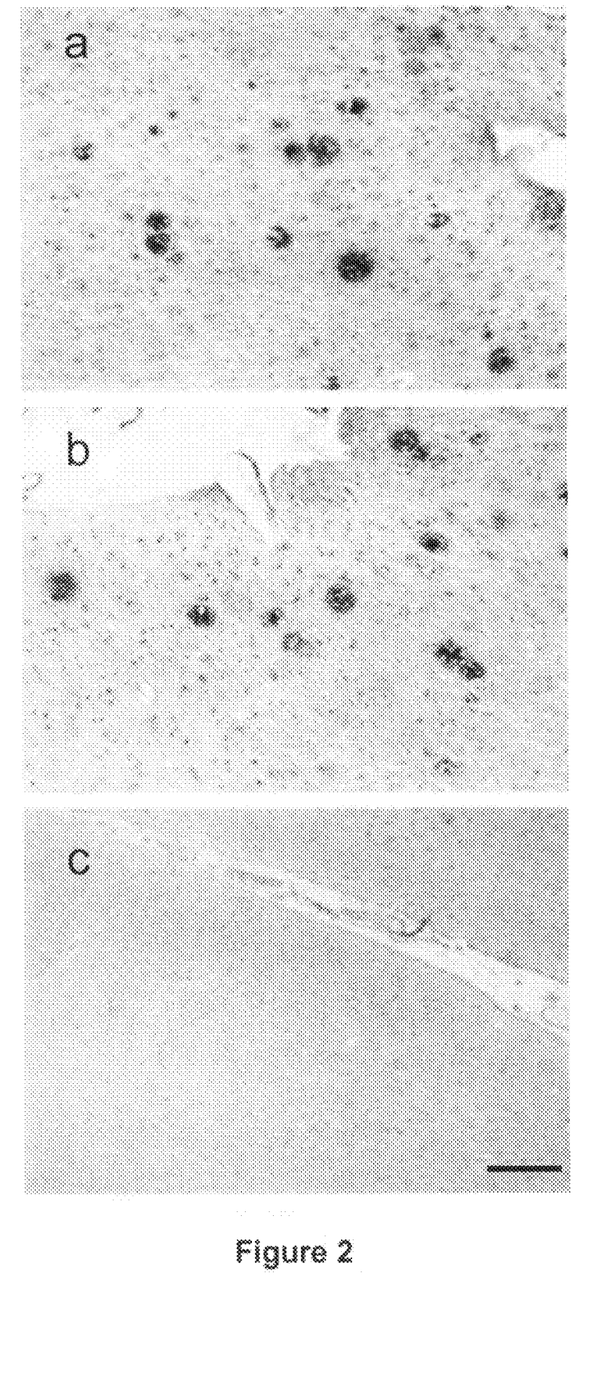

As shown in FIG. 2a-b, sera from mice immunized with the tetrameric or the octameric form of Trx(Aβ1-15)n, bound to amyloid plaques up to a dilution of 1/1000.

Large neuritic plaques, as well as mature and immature plaques, were labelled by antimultimeric Trx(Aβ1-15)n antibodies. A broader immunostaining, especially within senile plaque cores, was observed with the positive control anti-Pan β-amyloid antiserum, generated in rabbits using Aβ40 as antigen (not shown). By comparison, no plaques were detected either with sera from mock-treated animals (not shown), or with sera from mice immunized with monomeric TrxAβ1-15 (FIG. 2c).

Figure 3:
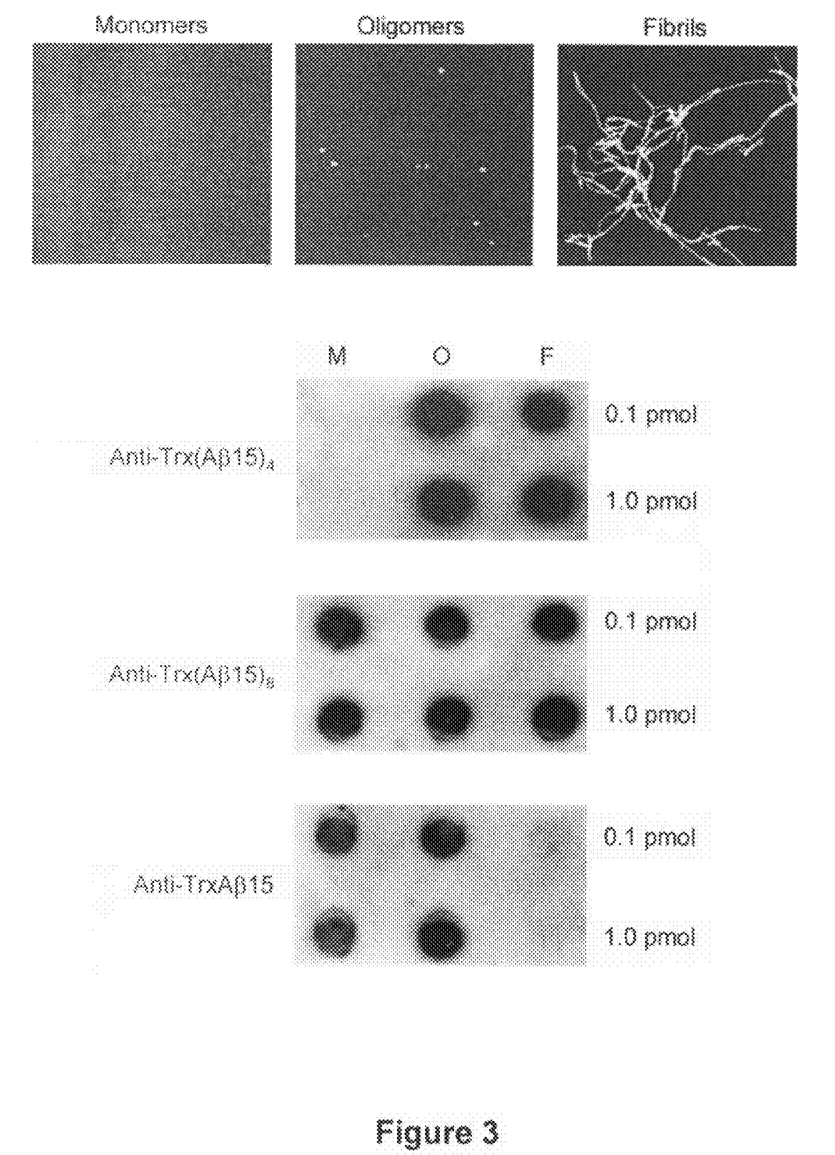
FIG. 3 shows AFM images showing preferential bindings of immunogens according to embodiments of the present invention.

Finally, immunoblots were used to assess the capacity of the various anti-Trx(Aβ1-15)n antibodies toward different assembly states of Aβ42 (monomers, oligomers and fibrils) generated in vitro under previously determined conditions and verified by atomic force microscopy (AFM). The results of this analysis are given in FIG. 3, which shows that anti-Trx(Aβ1-15)8 antibodies bind all three Aβ42 species, while anti-Trx(Aβ1-15)4 antibodies preferentially bind both soluble oligomers and fibrils, but not Aβ42 monomers. In sharp contrast, antibodies raised against the monomeric TrxAβ1-15 antigen shows no binding as well as lack of recognition of Aβ42 fibrils. The latter observation is in accordance with the inability of these antibodies to recognize higher order Aβ42 aggregates in ELISAs as well as Aβ fibrils in AD plaques (see FIGS. 1c and 2c). Interestingly, however, anti-monomeric TrxAβ1-15 antibodies bind Aβ42 monomers and oligomers (FIG. 3). Trx(Aβ1-15)4 is thus a soluble, T cell epitope-lacking amyloid-β derivative with good immunogenic activity, even when formulated with a moderate-strength adjuvant such as alum, Al(OH)3. Also significant is the ability of Trx(Aβ1-15)4 to generate antibodies that bind to synaptotoxic Aβ42 oligomers and fibrils, but not to the presumably physiological monomeric Aβ species.

The main advantages of Trx-dPI compared to other peptide immunization strategies are its time and cost effectiveness, the lack of cellular toxicity and the yield of chemically homogeneous immunoconjugates, the batch-to-batch consistency of which can be readily verified. Moreover, once a "lead antigen" has been identified, it is easily amenable to further modification, including the incorporation of additional peptide epitopes and vector replacement for DNA vaccination purposes.

TrxAβ constructs. The sequence coding for E. coli thioredoxin has been amplified by polymer chain reaction (PCR) employing primers 1 and 2 (Table 2), design to confer the restriction site NdeI e BamHI. The amplified fragment has been double digested with NdeI e BamHI restriction enzymes and ligated to pET28b® (Novagen) digested with the same two enzymes; the resulting vector, designed as pT7Kan-Trx, harbors the sequence for an N- and C terminally His6-tagged (SEQ ID NO: 15) version of bacterial thioredoxin along with a kanamicin resistance marker.

The unique CpoI site present within the Trx coding sequence (nucleotide positions 99-105, corresponding to amino acid residues 34-35, identified as: 5' . . . CG/GT(A)CCG . . . 3') was used as cloning site.

Instrumental to the production of multimers are the directionality and in-frame fusion capabilities of the unique CpoI site.

pT7Kan-TrxAβ1-15. The sequence coding for the Aβ1-15 peptide, the N-terminal fragment of the amyloid beta peptide Aβ42, has been obtained by annealing of the phosphorylated oligonucleotides:

(SEQ ID NO: 16)
5'-GTCCGATGGATGCAGAATTCCGACATGACTCAGGATATGAAGTTCAT

CATCAAGGCG-3' (forward)

(SEQ ID NO: 17)
3'-GCTACCTACGTCTTAAGGCTGTACTGAGTCCTATACTTCAAGTAGTA

GTTCCGCCAG-5' (reverse)

bearing a terminal CpoI recognition sequence. The DNA insert of 57 bp (5'-protruding CpoI) has been ligated to CpoI-digested pT7Kan-Trx, at 1/10 vector/insert molar ratio.

N-n4-6xHis (SEQ ID NO: 15)-n10-TRX(1-33) GP MDAEFRHDSGYEVHHQGGPTRX (Residues 54-74 of SEQ ID NO: 18) (36-109)-n15-6xHis (SEQ ID NO: 15)-C The entire sequence is:

(SEQ ID NO: 18)
mgsshhhhhhssglvprgshMGDKIIHLTDDSFDTDVLKADGAILVDFWA

EWCGPMDAEFRHDSGYEVHHQGGPCKMIAPILDEIADEYQGKLTVAKLNI

DQNPGTAPKYGIRGIPTLLLFKNGEVAATKVGALSKGQLKEFLDANLRdp nsssvdklaaalehhhhhh.

The main features of the TrxAβ1-15 construct concern with the presence of a Met residue (M) at the N-terminus of Aβ115 peptide, a Gly-Gly-Pro linker at the C-terminus of Aβ115 peptide and sequences coding for an N- and a C-terminally His$_6$-tagged (SEQ ID NO: 15) version of bacteria thioredoxin.

pT7Kan-Trx(Aβ1-15)$_4$ e pT7Kan-Trx(Aβ1-15)$_8$. Constructs bearing more copies of Aβ115 peptide have been obtained in a similar way, but at 1/100 vector/insert molar ratio. Recombinant clones were screened by restriction digestion/gel electrophoresis and two of them bearing four or eight copies of the Aβ115 sequence were used to express and purify the corresponding recombinant proteins Trx(Aβ1-15)$_4$ and Trx(Aβ1-15)$_8$.

The presence of two His$_6$-tag (SEQ ID NO: 15) helps the purification step and could increase the immunogenicity, as the case of tandem repeats of lysine residues.

TABLE 2

| N° | Primer Name | Sequence | $T_m$ |
|---|---|---|---|
| 1 | Nde_Trx-PLUS | Cgcatatgggcgataaaattattcacc (SEQ ID NO: 19) | 60 |
| 2 | Bam_Trx-MINUS | Cgggatcccgccaggttagcgtcgag (SEQ ID NO: 20) | 60 |

Expression and purification of the Trx Aβ polypeptides. Expression was induced by adding 1 mM isopropyl-β-D-thiogalactopyranoside (IPTG) to E. coli BL21Star (DE3) cells (Invitrogen) transformed with each of the above constructs and allowed to proceed for 2 h at 37° C. A different E. coli strain (Origami-DE3; Novagen) and modified expression conditions (pT7-Amp-Trx vector; 5 h at 30° C.) were used for Trx Aβ42, which was otherwise completely insoluble. Following cell lysis, His6-tagged (SEQ ID NO: 15) Trx Aβ polypeptides were bound to a metal-affinity resin (Talon; Clontech), purified as per manufacturer instructions and extensively dialyzed against phosphate buffered saline (PBS). Protein concentration was determined with the Coomassie dye method (Bio-Rad) and by UV absorbance. The composition and purity of individual polypeptides was assessed by both gel electrophoresis on 11% polyacrylamide-SDS gels and MALDI-TOF analysis (MassLynx 4.0, Waters).

Immunization protocol. Recombinant Trx Aβ polypeptides (2 mg/ml in PBS) were filter-sterilized and an aliquot of each (10 nmol) was mixed with 1 mg of alum (Sigma-Aldrich), in a final volume of 400 µl, immediately before use. Aβ42 (Sigma-Aldrich) was dissolved in PBS (2 mg/ml) and aggregated overnight at 37° C. prior to immunization. Five randomly assorted groups of one-month-old, male BALB/c mice (Charles River Laboratories; 10 animals each) were injected subcutaneously with the above antigens at day 1, 15, 30 and 60, as specified in FIG. 1c. The same treatment was applied to two negative control groups that were injected with PBS and with aggregated Aβ42, both without alum. Sera were collected two weeks after the last boost and randomly pooled in pairs.

Detection of anti-Aβ42 antibodies. Total anti-Aβ42 antibodies were detected by ELISA at a fixed 1/200 dilution, using aggregated Aβ42 (0.5 µg/well) as the target antigen23. Following incubation, washing, and the addition of horseradish peroxidase (HRP)-conjugated anti-mouse immunogloburns (1/5000; sigma-Aldrich) and chromogenic substrate o-phenylendiamine (Sigma-Aldrich), plates were read spectrophotometrically at 450 nm. Immunoglobulin isotype determination was conducted at a fixed 1/200 dilution, using rat anti-mouse Ig subclass-specific, HRP-conjugated secondary antibodies (TechniPharm). ELISAs were conducted in triplicate on the five-paired sera from each group; only a subset of sera from the three top responders in groups 1, 3, 4, 6 and 7 (FIG. 1c) was utilized for isotype determination. Comparisons between groups were conducted by one-way ANOVA using the Analyze-it software.

Immunohistochemistry. Sera from mice immunized with each of the three TrxAβ1-15 polypeptides were screened for their ability to bind Aβ plaques in human brain sections from a 68-year-old patient with neuropathological and clinical symptoms typical of severe Alzheimer's disease. Various dilutions (1/100-1/1000) of pooled sera from the three top responders in groups 5, 6 and 7 were analyzed; the best results were obtained with a 1/500 dilution. Sera were added to serial 8-µm brain sections of formalin-fixed, temporal cortical tissue, pre-treated with formic acid (80%, 15 min). Sera from mock-treated (PBS) animals and a commercial anti-Aβ40 polyclonal antibody preparation (Anti-Pan β-Amyloid, Biosource) were used as negative and positive controls, respectively. Immunolabeling was revealed with the EnVision Plus/horseradish peroxidase system (Dako), using 3-3'-diaminobenzidine as the chromogenic substrate according to manufacturer instructions.

Images were captured with a digital camera at magnifications ranging from 50 to 400×.

Dot blot assays and AFM imaging. Aβ42 species for dot blot analysis were prepared according to previously protocols known in the art (see for example Stine, W. B. et al in J. Biol. Chem. Volume 278, page 11612-11622). Briefly, Aβ42 dissolved in 2 M DMSO (1 mM final concentration) was utilized as the source of the monomeric form; dilution of the DMSO stock solution into cold Ham's F12 K medium (phenol red-free; Biosource) at a final concentration of 100 µM, followed by incubation for 24 h at 4° C. was used to prepare soluble oligomers; the same stock solution diluted into 10 mM HCl at a final concentration of 100 µM and incubated for 24 h at 37° C. was used to generate Aβ fibrils. The identity of the various Aβ species, as well as the absence of fibrils from soluble oligomer solutions, was verified by AFM. To this end, the above-described Aβ42 solutions were diluted 10-fold in 20 µl of deposition buffer (4 mM HEPES pH 7.4, 10 mM NaCl, 7 mM MgCl2) to a final concentration of 10 µM and immediately deposited onto freshly cleaved ruby mica at room temperature. After five minutes, mica disks were rinsed with milli-Q grade water and gently dried under a stream of nitrogen. Images were collected with a Nanoscope III microscope (Digital Instruments) operated in tapping mode, using commercial diving board silicon cantilevers (MikroMasch). A fixed volume of each Aβ species, corresponding to either 0.1 pmol or 1 pmol of Aβ42 peptide, was spotted onto nitrocellulose membranes (GE Healthcare Life Sciences) pre-wetted with 20 mM Tris-HCl, pH 7.5, 0.8% NaCl (TBS) using a vacuum-operated dot blotter apparatus (96 wells; Bio-Rad). Dot blots were prepared in batches of eight membranes each, which were dried and stored at 4° C. for no more than two weeks before use. Antisera for dot blot analysis were affinity-purified on protein-A minicolumns (Diatheva) as per manufacturer instructions. Following determination of total immunoglobulin concentration with the Coomassie dye method, purified immunoglobulins were used for dot blot assays at a final concentration of 0.75 µg/ml. After blocking at room temperature with 5% non-fat dry milk in TBS supplemented with 0.05% Tween 20 (TBST), blots were incubated for 1.5 hours with each of the three primary Trx Aβ1-15 antibodies in dry milk-TBST, washed 3×10 min with TBST, followed by mouse immunoglobulin detection with the SuperSignal West Femto kit (Pierce) as specified by the manufacturer. Three independent technical replicates were carried with antisera from the top responding pool in each group.

EXAMPLE 2

Evaluation of the Effects of Anti-Trx(Aβ1-15)$_4$ Antibodies in vivo on Brain β-amyloid Pathology in Adult Tg2576 Transgenic Mice Methods Female transgenic AD (Tg2576) mice expressing the Swedish mutation of human APP (1) were obtained from Boston University Alzheimer's Disease Center's mouse colony. Founders for this colony were provided by Dr. Karen Hsiao-Ashe (Department of Neurology, University of Minnesota Medical School). APP Tg2576 mice develop behavioural abnormalities and exhibit histological evidence of brain Aβ deposits as plaques, along with associated astrogliosis, from as early as 8 months. Mice were genotyped using a standardized PCR assay on tail DNA and were housed four in each cage under standard conditions with ad libitum access to food and water. Six 14-month-old APP mice (32-34 g each), placed on a 12 hr light schedule, were used for surgeries. Mice were anesthetized with ketamine HCl/xylazine intraperitoneal injection (100 mg/kg ketamine and 10 mg/kg xylazine; 100 µl/10 g body weight) and were positioned in a stereotaxic apparatus (Koph) with a mouse head adaptor. Thermoregulation was maintained at 37° C. using a warming pad with respiratory monitoring throughout the procedure. The scalp was incised in the midline to expose the sagittal suture and stereotaxic coordinates in both hemispheres were determined (2). The bregma was used as reference point (2.0 mm) and holes were drilled in the calvarium at the junction of the left and right lateral coordinates (1.75 mm). Affinity-purified anti-Trx(Aβ1-15)$_4$ antibodies along with mock immunoglobulins from PBS-treated mice (2 μl each) were stereotaxically injected into the left and right hippocampus (2.0 mm ventral), respectively, using a blunt-tipped 10 μl syringe (Hamilton). Upon syringe placement there was a 2 min dwell time, followed by a 4 min injection time and an additional 2 min dwell time prior to removal of the syringe. A topical antiseptic was applied as the incision was closed, using a 9 mm autoclip. Mice were kept on a warming pad until full recovery. All animal experiments were performed in accordance with the National Institutes of Health Guide for the Care and Use of Laboratory Animals and both the Veterans Administration and Boston University Animal Care Committees. Seven days post-injection, mice were deeply anesthetized and transcardially perfused with 2% buffered paraformaldehyde (100 ml). Brains were post-fixed for 2 h, cryoprotected in a graded series of glycerol and subsequently frozen-sectioned (50 μm). Serially cut mouse tissue sections were stained for Nissl substance, immunostained with anti-Aβ42 (cat. no. 344; Biosource International), anti-Aβ oligomer (A11; Biosource International) and glial fibrillary antigen protein (GFAP; Dako) antibodies, and silver stained using the Campbell-Switzer method for identification of mature Aβ plaques. Serial-cut Aβ42 immunostained coronal tissue-sections within the hippocampus beginning from Interaural: 1.68 mm/Bregma: −2.12 mm to Interaural: 2.16 mm/Bregma: −1.64 mm were quantitatively analyzed. Aβ42-positive plaques were quantified from high resolution images of the same brain areas within the anti-Trx(Aβ1-15)$_4$-treated hemisphere and the contralateral PBS-treated hemisphere using BioVision (3) and Neurolucida software programs (MicroBrightField, Williston, Vt.). BioVision differentiates and counts plaques from the background neuropil, while Neurolucida extracts the data from the BioVision images, exporting it to Excel (Microsoft, Redmond, Wash.) for statistical analysis.

Results

The immunotherapeutic potential of anti-Trx(Aβ1-15)$_4$ was evaluated next by stereotaxically injecting this antibody into the hippocampus of 14-month-old APP transgenic AD (Tg2576) mice. Mock immunoglobulins from mice treated with PBS only, injected into the contralateral hemisphere, served as an internal control for this experiment. Seven days post-injection, histopathological examination revealed a marked reduction of Aβ immunostaining in the hippocampus and overriding neocortex of mice receiving the anti-Trx(Aβ1-15)$_4$ antibody, in contrast to the mock-injected hemisphere. A β positive plaques were not only absent at the injection site, but significantly diminished within the injection penumbra (2 mm anterior/posterior to the injection site).

This suggests that not only fibrils and small oligomers, but also higher-order oligomers are targeted in vivo by the anti-Trx(Aβ1-15)$_4$ antibody. In order to verify that these findings were not the result of a competition between anti-Trx(Aβ1-15)$_4$ and the primary anti-Aβ antibody, we performed alternative histopathological analyses using glial fibrillary antigen protein (GFAP) immunostaining and Campbell-Switzer silver staining to detect astrogliosis and Aβ plaques. Astrogliosis and glia-associated plaques were markedly reduced within the anti-Trx(Aβ1-15)$_4$ antibody injection penumbra compared to the contralateral mock-injected hemisphere. In addition, as revealed by Campbell-Switzer silver staining, there were far less plaques in the anti-Trx(Aβ1-15)$_4$-injected hemisphere compared to the mock-injected hemisphere. Both observations are consistent with the immunostaining data obtained with anti-Aβ antibody detection. From a quantitative point of view, in comparison to the PBS-treated hemisphere, there was a significant reduction in the number of Aβ42-positive plaques in the anti-Trx(Aβ1-15)$_4$-treated hemisphere (PBS-treated hemisphere: $3.34 \times 10^3 \pm 0.58$; anti-Trx(Aβ1-15)$_4$-treated hemisphere: $0.97 \times 10^3 \pm 0.27$, P<0.01).

The invention claimed is:

1. An immunogenic construct comprising a carrier, said carrier bearing at least one fragment of Aβ42 within an active loop site of the carrier.

2. The immunogenic construct of claim 1, wherein the Aβ42 fragment is bound to the carrier by means of an amino acid linker.

3. The immunogenic construct of claim 1, wherein the carrier is thioredoxin.

4. The immunogenic construct of claim 3, wherein said at least one Aβ42 fragment is a N-terminal fragment of less than 30 amino acid residues.

5. The immunogenic construct of claim 3, wherein the at least one Aβ42 fragment is selected from the group consisting of Aβ1-3, Aβ1-4 (SEQ ID NO: 3), Aβ1-5 (SEQ ID NO: 4), Aβ1-6 (SEQ ID NO: 5), Aβ1-7 (SEQ ID NO: 6), Aβ1-8 (SEQ ID NO: 7), Aβ1-9 (SEQ ID NO: 8), Aβ1-10 (SEQ ID NO: 9), Aβ1-11 (SEQ ID NO: 10), Aβ1-12 (SEQ ID NO: 11), Aβ1-13 (SEQ ID NO: 12), Aβ1-14 (SEQ ID NO: 13), and Aβ1-15 (SEQ ID NO: 14).

6. The immunogenic construct of claim 5, wherein the at least one Aβ42 fragment is Aβ1-15 (SEQ ID NO: 14).

7. The immunogenic construct of claim 6, wherein the Aβ1-15 (SEQ ID NO: 14) fragment is bound to the thioredoxin by means of an amino acid linker.

8. The immunogenic construct of claim 7, wherein the amino acid linker is Gly-Gly-Pro.

9. The immunogenic construct of claim 6, wherein the thioredoxin bears more than one said Aβ1-15 (SEQ ID NO: 14) fragment.

10. The immunogenic construct of claim 9, wherein the thioredoxin bears 4 to 16 said Aβ1-15 (SEQ ID NO: 14) fragments.

11. The immunogenic construct of claim 10, wherein the thioredoxin bears four Aβ1-15 (SEQ ID NO: 14) fragments (Trx(Aβ1-15)$_4$).

12. The immunogenic construct of any one of claims 9 to 11, wherein each said Aβ1-15 (SEQ ID NO: 14) fragment is bound to the thioredoxin by means of the amino acid linker.

13. The immunogenic construct of claim 12, wherein the amino acid linker is Gly-Gly-Pro.

14. A pharmaceutical composition for use as a therapeutic vaccine against amyloidogenic diseases, said composition comprising an immunogenic construct comprising a carrier, said carrier hearing at least one fragment of Aβ42 within an active loop site of said carrier.

15. The pharmaceutical composition of claim 14, wherein the carrier is thioredoxin.

16. The pharmaceutical composition of claim 15, wherein the Aβ42 fragment is bound to the carrier by means of an amino acid linker.

17. The pharmaceutical composition of claim 15, wherein said at least one Aβ42 fragment is a N-terminal fragment of less than 30 amino acid residues.

18. The pharmaceutical composition of claim 15, wherein said at least one Aβ42 fragment is selected from the group consisting of Aβ1-3, Aβ1-4 (SEQ ID NO: 3), Aβ1-5 (SEQ ID NO: 4), Aβ1-6 (SEQ ID NO: 5), Aβ1-7 (SEQ ID NO: 6), Aβ1-8 (SEQ ID NO: 7), Aβ1-9 (SEQ ID NO: 8), Aβ1-10 (SEQ ID NO: 9), Aβ1-11 (SEQ ID NO: 10), Aβ1-12 (SEQ ID NO: 11), Aβ1-13 (SEQ ID NO: 12), Aβ1-14 (SEQ ID NO: 13), and Aβ1-15 (SEQ ID NO: 14).

19. The pharmaceutical composition of claim 18, wherein the at least one Aβ42 fragment is Aβ1-15 (SEQ ID NO: 14).

20. The pharmaceutical composition of claim 19, wherein the Aβ1-15 (SEQ ID NO: 14) fragment is bound to the thioredoxin by means of an amino acid linker.

21. The pharmaceutical composition of claim 20, wherein the amino acid linker is Gly-Gly-Pro.

22. The pharmaceutical composition of claim 19, wherein the thioredoxin bears more than one said Aβ1-15 (SEQ ID NO: 14) fragment.

23. The pharmaceutical composition of claim 22, wherein the thioredoxin bears 4 to 16 said Aβ1-15 (SEQ ID NO: 14) fragments.

24. The pharmaceutical composition of claim 23, wherein the thioredoxin bears 4 said Aβ1-15 (SEQ ID NO: 14) fragments.

25. The pharmaceutical composition of claim 24, wherein each said Aβ1-15 (SEQ ID NO: 14) fragment is bound to the thioredoxin by means of the amino acid linker.

26. The pharmaceutical composition of claim 25, wherein the amino acid linker is Gly-Gly-Pro.

27. The pharmaceutical composition of claim 14, further comprising an adjuvant.

28. The pharmaceutical composition of claim 27, wherein the adjutant is selected from the group consisting of 3 De-O-acylated monophosphoryl lipid A (MPL), the saponin QS21, muramyl-di-peptide and an aluminum salt.

29. The pharmaceutical composition of claim 28, wherein the aluminum salt is selected from the group consisting of aluminum hydroxide, aluminum phosphate and aluminum sulfate.

30. An immunogenic construct comprising a carrier, said carrier bearing at least one fragment of Aβ42 within an active loop site of said carrier, wherein said immunogenic construct is produced by the method comprising
  i) amplifying the carrier in a suitable bacterium,
  ii) inserting the carrier in a suitable vector, said vector comprising a T7 promoter for the protein expression throughout the pET system;
  iii) preparing an Aβ fragment DNA insert; and
  iv) restricting and ligating the carrier-vector and the Aβ fragment DNA insert.

* * * * *

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Pro Gly Pro Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Gly Ser Gly
1
```

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Ala Glu Phe
  1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ala Glu Phe Arg
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Glu Phe Arg His
  1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Ala Glu Phe Arg His Asp
  1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ala Glu Phe Arg His Asp Ser
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 8

Asp Ala Glu Phe Arg His Asp Ser Gly
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ala Glu Phe Arg His Asp Ser Gly Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Ala Glu Phe Arg His Asp Ser Gly Tyr Glu
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ala Glu Phe Arg His Asp Ser Gly Tyr Glu Val
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ala Glu Phe Arg His Asp Ser Gly Tyr Glu Val His
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ala Glu Phe Arg His Asp Ser Gly Tyr Glu Val His His
1               5                   10

<210> SEQ ID NO 14
<211> LENGTH: 15
<212> TYPE: PRT
```

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Asp Ala Glu Phe Arg His Asp Ser Gly Tyr Glu Val His His Gln
1               5                   10                  15

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 15

His His His His His His
1               5

<210> SEQ ID NO 16
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
gtccgatgga tgcagaattc cgacatgact caggatatga agttcatcat caaggcg            57

<210> SEQ ID NO 17
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
gctacctacg tcttaaggct gtactgagtc ctatacttca agtagtagtt ccgccag            57

<210> SEQ ID NO 18
<211> LENGTH: 169
<212> TYPE: PRT
<213> ORGANISM: Artificial Sequence
<220> FEATURE:
<223> OTHER INFORMATION: Description of Artificial Sequence: Synthetic
construct

<400> SEQUENCE: 18

Met Gly Ser Ser His His His His His His Ser Ser Gly Leu Val Pro
1               5                   10                  15

Arg Gly Ser His Met Gly Asp Lys Ile Ile His Leu Thr Asp Asp Ser
                20                  25                  30

Phe Asp Thr Asp Val Leu Lys Ala Asp Gly Ala Ile Leu Val Asp Phe
            35                  40                  45

Trp Ala Glu Trp Cys Gly Pro Met Asp Ala Glu Phe Arg His Asp Ser
        50                  55                  60

Gly Tyr Glu Val His His Gln Gly Gly Pro Cys Lys Met Ile Ala Pro
65                  70                  75                  80

Ile Leu Asp Glu Ile Ala Asp Glu Tyr Gln Gly Lys Leu Thr Val Ala
                85                  90                  95

```
                                                            -continued

Lys Leu Asn Ile Asp Gln Asn Pro Gly Thr Ala Pro Lys Tyr Gly Ile
            100                 105                 110

Arg Gly Ile Pro Thr Leu Leu Phe Lys Asn Gly Glu Val Ala Ala
        115                 120                 125

Thr Lys Val Gly Ala Leu Ser Lys Gly Gln Leu Lys Glu Phe Leu Asp
    130                 135                 140

Ala Asn Leu Arg Asp Pro Asn Ser Ser Ser Val Asp Lys Leu Ala Ala
145                 150                 155                 160

Ala Leu Glu His His His His His His
                165

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgcatatggg cgataaaatt attcacc                                         27

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgggatcccg ccaggttagc gtcgag                                          26
```